United States Patent
Peng et al.

(10) Patent No.: US 10,029,996 B2
(45) Date of Patent: Jul. 24, 2018

(54) CLASS OF CYANO-SUBSTITUTED ASYMMETRIC CYANINE DYES, SYNTHESIZING METHOD AND APPLICATION THEREOF

(71) Applicant: DALIAN UNIVERSITY OF TECHNOLOGY, Dalian, Liaoning (CN)

(72) Inventors: Xiaojun Peng, Liaoning (CN); Si Zhang, Liaoning (CN); Jiangli Fan, Liaoning (CN); Jingyun Wang, Liaoning (CN)

(73) Assignee: DALIAN UNIVERSITY OF TECHNOLOGY, Dalian, Liaoning (CN)

( * ) Notice: Subject to any disclaimer, the term of this patent is extended or adjusted under 35 U.S.C. 154(b) by 789 days.

(21) Appl. No.: 14/486,210

(22) Filed: Sep. 15, 2014

(65) Prior Publication Data
US 2015/0118703 A1    Apr. 30, 2015

(30) Foreign Application Priority Data
Oct. 30, 2013    (CN) .......................... 2013 1 0530150

(51) Int. Cl.
| | | |
|---|---|---|
| *C07D 417/06* | (2006.01) | |
| *C07D 277/64* | (2006.01) | |
| *C07D 215/10* | (2006.01) | |
| *G01N 1/30* | (2006.01) | |

(52) U.S. Cl.
CPC ......... *C07D 277/64* (2013.01); *C07D 215/10* (2013.01); *C07D 417/06* (2013.01); *G01N 1/30* (2013.01)

(58) Field of Classification Search
CPC ..................................................... C07D 417/06
USPC ........................................................ 546/165
See application file for complete search history.

(56) References Cited

U.S. PATENT DOCUMENTS

2009/0017441 A1*    1/2009    Peng ....................... C09B 23/06
                                                                 435/4

OTHER PUBLICATIONS

Zhang et al., "A bright red, etc.," J. Mater. Chem. B, 2014, 2, 2688-2693.*

* cited by examiner

*Primary Examiner* — Patricia L Morris
(74) *Attorney, Agent, or Firm* — Novick, Kim & Lee, PLLC; Allen Xue

(57) ABSTRACT

The present invention provides a category of cyano-substituted asymmetric cyanine dyes having the following general structural Formula I and its synthesizing method. The cyano-substituted asymmetric cyanine dyes in present invention are easily synthesized and have long emission wavelength, high molar extinction coefficient, high sensitivity, good light stability, high fluorescence quantum yield after binding with nucleic acid, and low cell toxicity, which is beneficial for application as fluorescent dyes and could also be used in the field of identifying nucleic acid molecules, clinical diagnostics, and immunoassay testing etc.

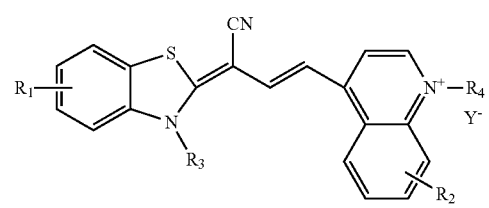

5 Claims, 3 Drawing Sheets

CLASS OF CYANO-SUBSTITUTED ASYMMETRIC CYANINE DYES, SYNTHESIZING METHOD AND APPLICATION THEREOF

FIELD OF THE INVENTION

The present invention relates to a novel category of fluorescent dyes, their synthesizing methods and applications in fine chemical domains, particularly a category of cyano-substituted asymmetric cyanine dyes, their synthesizing methods and application utilizing the mentioned cyanine dyes, their conjugates or compositions for biological staining.

BACKGROUND OF THE INVENTION

Fluorescent dyes as functional pigments have been widely used in various fields of science and technology. Especially research on them in the life sciences, clinical diagnostics, immunoassay testing and other aspects has been the world's attention. At present, phenanthridines (EB, PI), acridines (AO), imidazoles (Hoechst, DAPI), cyanine dyes (Cy, TOTO, SYTO) and other commercially available fluorescent dyes have played significant role in the fields of genomics, quantitative detection of nucleic acids, blood cell analysis and etc. However, all these commercially available fluorescent dyes have their own application limitations. Most of them are impermeable and not suitable for live-cell imaging. Only a few of them such as Hoechst and SYTO are suitable for live-cell imaging. Hoechst33258 and Hoechst34580 are the most commonly used probes, but they emit blue fluorescence upon binding to DNA. As the UV light damages cellular DNA, protein and other components, the use of them is very restricted in time [S. K. Davis, C. J. Bardeen, Photochem. Photobiol. 2003, 77, 675-679]. Besides, it's difficult for excitation light to penetrate into the inside biological tissues due to the strong absorption of ultraviolet light by some components in biological samples. Furthermore, the self fluorescence of some biological components may lead to a high fluorescence background that interferes with detection. The class of SYTO compounds show small Stokes shift, which causes the background interference and fluorescence self-quenching. Moreover, due to the traditional cyanine dye structure of SYTO, the defect of their stability can not be ignored. Therefore, exploring novel fluorescent dyes meeting the multiple criteria of excellent spectral properties (e.g. excellent photostability, large Stokes shift), low toxicity and live cell permeability is still the key to promote the development of fluorescent analysis technology, life science and other fields.

Therefore, it is still in great demand to develop of novel fluorescent dyes with the following characteristics: showing low fluorescence background in the absence of nucleic acids, high quantum yield upon binding to nucleic acids and no affinity for biomolecules except for nucleic acids; having excellent photostability, as well as good live cell permeability; exhibiting spectral range with obvious discrepancy from that of biological samples.

SUMMARY OF THE INVENTION

Firstly, against the inadequacies in existing technologies, such as low cell-permeability, restricted by optical excitation time, low detection efficiency and so on, the present invention provides a novel category of compounds with simple structure, high sensitivity, excellent photostability, high fluorescence quantum yield and live cell permeability.

Secondly, the present invention further provides a method for synthesizing the above mentioned compounds.

Thirdly, the present invention provides the application of the above mentioned compounds as fluorescent dye.

To achieve the above technical object, the present invention employs the following technical solutions;

An cyano-substituted asymmetric cyanine compounds having a general Formula I as follow:

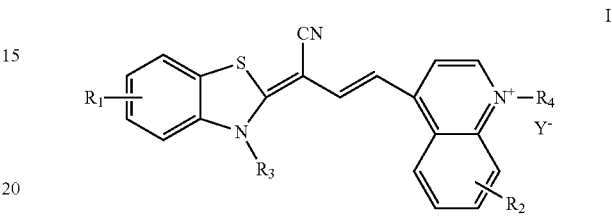

wherein $R_1$ and $R_2$ are each independently selected from the group consisting of H, $C_{1-18}$ saturated alkyl, $C_{1-18}$ unsaturated alkyl, $OR_5$ and halogen;

$R_3$ and $R_4$ are each independently selected from the group consisting of $C_{1-6}$ saturated alkyl, $C_{1-6}$ unsaturated alkyl and $-CH_2CH_2OR_5$;

$R_5$ is selected from the group consisting of H and $C_{1-6}$ alkyl;

$Y^-$ is a halogen ion.

In preferred embodiments of the invention, $R_1$ and $R_2$ are independently selected from the group consisting of H, OR5 and halogen; $R_3$ and $R_4$ are independently selected from the group consisting of saturated $C_{1-4}$ alkyl, unsaturated $C_{1-4}$ alkyl and $-CH_2CH_2OR_5$, $R_5$ is selected from the group consisting of H and $C_{1-2}$ alkyl.

In above-mentioned embodiments of the invention, $R_3$ is more preferably selected from the group consisting of saturated $C_{1-4}$ alkyl and $-CH_2CH_2CH=CH_2$; $R_4$ is more preferably selected from the group consisting of $C_{1-2}$ alkyl and $-CH_2CH_2OH$;

In preferred embodiments of the invention, the cyano-substituted asymmetric cyanine dyes are selected from compounds C, D and E.

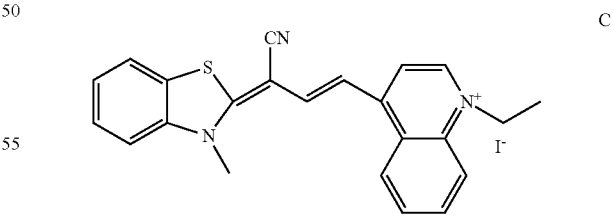

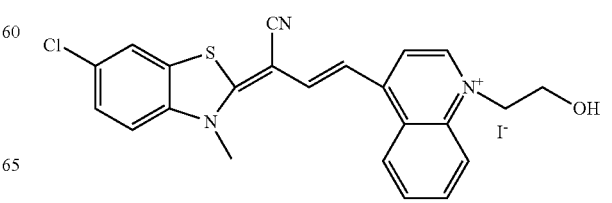

-continued

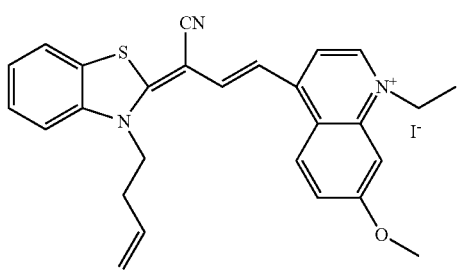

E

In another aspect, the present invention further provides a method for synthesizing the above-mentioned cyano-substituted asymmetric cyanine dyes which includes the following steps:

1) synthesis of the first intermediate: synthesizing the first intermediate having the general formula III by reacting a compound having the general formula II with compound $R_4Y$;

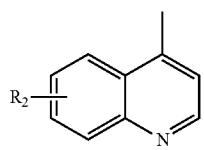

II

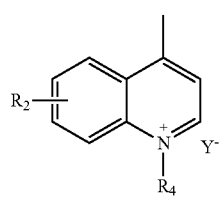

III 2) synthesis of the second intermediate: synthesizing the compound having the general formula V by reacting a compound having the general formula IV with $R_3Z$; wherein Z is halogen anion generated in the reaction or OTs⁻;

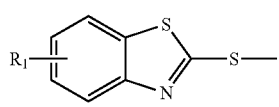

IV

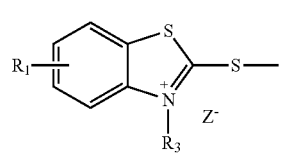

V 3) introducing cyano group into compound V: synthesizing the compound having the general formula VI by reacting the compound V obtained in the step 2) with cyanoacetate;

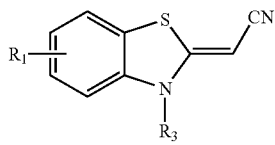

VI 4) introducing aldehyde group into compound VI: synthesizing the compound having the general formula VII by reacting the compound VI obtained in the step 3) with phosphorus oxychloride;

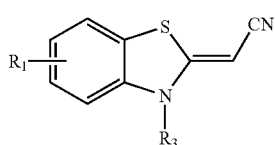

VII 5) synthesis of cyano-substituted asymmetric cyanine dyes: synthesizing the cyano-substituted asymmetric cyanine dyes by reacting the first intermediate III obtained in the step 1) with the compound VII obtained in the step 4) in solvent-free condition.

In above-mentioned method for synthesizing the cyano-substituted asymmetric cyanine dyes, the reaction of step 1) is carried out in the following conditions: compound II and $R_4Y$ are dissolved in a polar organic solvent with the molar ratio of 1:1-1:10, keeping the temperature at 60-180° C., and reacted for 4-48 h to obtain the first intermediate III.

The reaction condition of step 2) is as follows: compound IV and $R_3Z$ are dissolved in a polar organic solvent with the molar ratio of 1:1-1:10, and reacted for 4-48 h at 60-180° C. to obtain compound of formula V.

The above-mentioned polar organic solvent in step 1) and 2) both are selected from dichloromethane, chloroform, ethanol, acetonitrile, ethyl acetate, toluene, xylene o-dichlorobenzene or mixtures thereof.

The reaction condition of step 3) is as follows: compound V obtained in the step 2) and cyanoacetate are dissolved in a polar organic solvent with the molar ratio of 1:1-1:10 and reacted at 60-180° C. for 0.5-10 h to obtain compound VI.

VI

The polar organic solvent mentioned in step 3) is selected from pyridine, piperidine, chloroform, ethanol, acetonitrile, ethyl acetate, toluene, xylene, o-dichlorobenzene or mixtures thereof.

The reaction condition of step 4) is as follows: compound VI obtained in the step 3) and cyanoacetate are dissolved in a polar organic solvent with the molar ratio of 1:1-1:5 and reacted at 0-120° C. for 1-10 h to obtain the compound having the general formula VII.

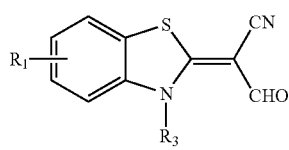

The polar organic solvent mentioned in step 3) is selected from N, N-dimethylformamide, pyridine, piperidine, chloroform, ethanol, acetonitrile, ethyl acetate, toluene, xylene, o-dichlorobenzene or mixtures thereof.

The reaction condition of step 5) is as follows: synthesizing the cyano-substituted asymmetric cyanine dyes by reacting the first intermediate III obtained in the step 1) with compound VII obtained in the step 4) in a molar ratio of 7:1-1:1 in solvent-free condition at 100-300° C. for 0.5-10 h.

In present invention, the compounds involved in different numbers each correspond to the structural formula with the same number.

The application of the cyano-substituted asymmetric cyanine dyes in present invention as fluorescent dyes.

The application of the cyano-substituted asymmetric cyanine dyes in present invention as fluorescent dyes. Especially, the compounds according to the present invention is particularly suitable for living cells staining, more specifically, for staining nucleus and nucleolar of living cells according to a conventional method.

The technical solution of the present invention has the following beneficial effects:

(1) Introduction of the cyano group into the cyano-substituted asymmetric cyanine dyes in present invention via methine chain that significantly improve the stability of the dye, increases the Stokes shift and the fluorescence quantum yield of the dyes, which will help to improve the signal to noise ratio.

(2) The cyano-substituted asymmetric cyanine dyes in present invention still have strong binding force after introducing the cyano group, and has good permeability into the cells, which is beneficial for detecting nucleic acids in vitro and cell imaging. These dyes have high molar extinction coefficient, high sensitivity and good light stability, and could be used for identifying nucleic acid molecules, clinical diagnostics, and immunoassay testing etc.

(3) The method for synthesizing the cyano-substituted asymmetric cyanine dyes in present invention has the advantages of simpleness. The products are easy to get with small cell toxicity and have greater potential applications in biological long-time observation.

BRIEF DESCRIPTION OF THE DRAWINGS

There are 7 drawings in this invention.

DETAILED DESCRIPTION OF PREFERRED EMBODIMENTS

Figure 1:
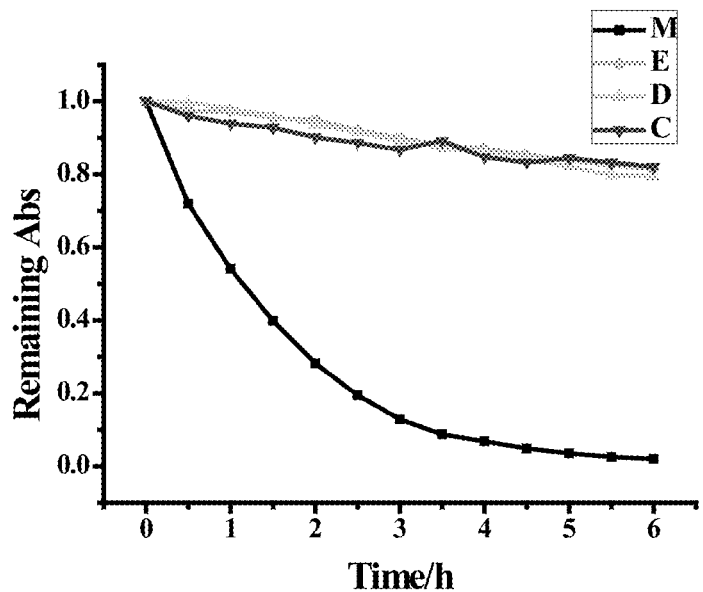
FIG. 1 is the comparisons of the photofading of compounds C, D, E in example 6 and reference compound M1 in Tris-HCl buffer.

The following non-limiting examples may enable one skilled in the field a more complete understanding of the present invention, but not limit the invention in any way.

To illustrate the optimization and improvement made by the introduction of CN group on dye performance, examples 6-12 use known compound M1 and commercially available dye SYTO9 as references. Wherein the structure of M1 is as follows:

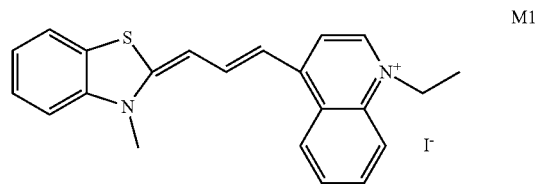 [SMILES: CC[n+]1ccc(/C=C/C=C2/Sc3ccccc3N2C)c2ccccc21 ; [I-]]

EXAMPLE 1

Synthesis of the Intermediate A1-hydroxyethyl-4-methylquinoline quaternary Ammonium Salt

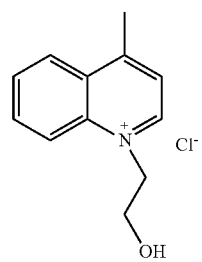

20 mmol of 4-methylquinoline and 60 mmol of chloroethanol are added under nitrogen protection into a round-bottom flask containing 20 mL toluene, and the reaction mixture is stirred and heated to reflux for 36 h. After the mixture cools down, the precipitate is filtered and the filter cake is washed with ethyl ether and dried to give a pale-yellow solid powder in a crude yield of 76%.

EXAMPLE 2

Synthesis of the Intermediate B

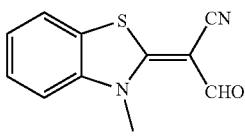

10 mmol of 1-methyl-2-methylsulphenyl benzothiazole quaternary ammonium salt (1-methyl-2-methylsulphenyl benzothiazole quaternary ammonium salt was synthesized with 2-methylsulphenyl benzothiazole and methyl iodide by general synthesis method of quaternary ammonium salt similar to that described in example 1) and 10 mmol cyanoacetate were added into a round-bottom flask containing 30 mL piperidine, then the mixture was stirred to dissolve, 14 mmol triethylamine was added dropwise to the reaction solution.

After overnight stirring of the resulting material, the mixture was slowly added to 300 mL water with stirring and a homogeneous solution was obtained followed by the precipitation of the product. The precipitate is filtered and the filter cake is washed with water and dried to give a khaki solid powder in a crude yield of 68%. A 6 mmol amount of phosphorus oxychloride was added dropwise to 10 mL dimethylformamide (DMF) in an ice bath, and a solution of 5 mmol of khaki intermediate synthesized previously in 10 mL DMF was added. The mixture was then stirred at 90° C. for 2 h under a nitrogen atmosphere. Then the mixture was cooled to room temperature and added to 200 mL ice-water mixture. NaOH was slowly added to the reaction flask with stirring during which time a homogeneous solution was obtained followed by the precipitation of the product. The solids were collected by filtration and washed thoroughly with water and dried to give a pale-yellow solid powder intermediate B in a crude yield 45%.

EXAMPLE 3

Synthesis of Compound C

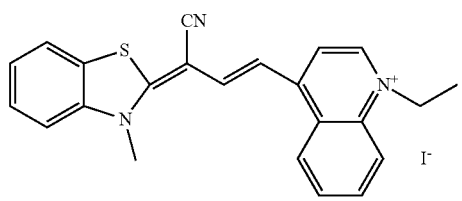

2 mmol of 1-ethyl-4-methylquinoline quaternary ammonium salt (1-ethyl-4-methylquinoline quaternary ammonium salt was synthesized with 4-methyl benzothiazole and ethyl iodide by general synthesis method of quaternary ammonium salt similar to that described in example 1) and 2 mmol of intermediate B were added into a 20 mL round-bottom flask, then the mixture was heated to 180° C. for 30 min under a nitrogen atmosphere and then allowed to cool. The mixture was purified by silica flash column chromatography using DCM(dichloromethane)/methanol(100:5) as an eluting solvent, and the red fraction was collected to obtain the title compound in a yield of 40%.

Product analysis: $^1$H NMR (400 MHz, DMSO) δ 8.99 (d, J=6.8, 1 H), 8.55 (d, J=8.0, 1 H), 8.39 (d, J=8.7, 1 H), 8.29 (d, J=6.8, 1 H), 8.21-8.11 (2 H, m), 8.01 (d, J=7.1, 1 H), 7.98-7.89 (1 H, m), 7.77 (d, J=8.2, 1 H), 7.60 (t, J=7.9, 1 H), 7.44 (t, J=8.0, 1 H), 7.19 (d, J=14.4, 1 H), 4.86 (q, J=7.3, 2 H), 4.12 (2 H, s), 1.54 (t, J=7.1, 3 H). $^{13}$C NMR (101 MHz, DMSO) δ=165.64, 145.52, 143.34, 141.86, 138.10, 137.02, 135.01, 129.02, 128.49, 125.88, 125.59, 124.89, 123.03, 119.28, 119.22, 118.08, 114.14, 114.11, 109.98, 75.89, 51.43, 36.70, 15.49.

EXAMPLE 4

Synthesis of Compound D

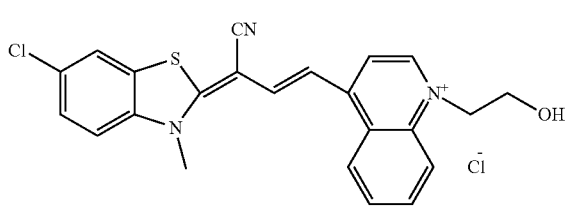

10 mmol of 1-methyl-5-chloro-2-methylsulphenyl benzothiazole quaternary ammonium salt (1-methyl-5-chloro-2-methylsulphenyl benzothiazole quaternary ammonium salt was synthesized with 5-chloro-2-methylsulphenyl benzothiazole and methyl iodide by general synthesis method of quaternary ammonium salt similar to that described in example 1) and 10 mmol cyanoacetate were added into a round-bottom flask containing 30 mL piperidine, then the mixture was stirred to dissolve, 14 mmol triethylamine was added dropwise to the reaction solution. After overnight stirring of the resulting material, the mixture was slowly added to 300 mL water with stirring and a homogeneous solution was obtained followed by the precipitation of the product. The precipitate is filtered and the filter cake is washed with water and dried to give a khaki solid powder in a crude yield of 68%.

A solution of 5 mmol of khaki intermediate synthesized previously in 10 mL DMF was added dropwise to the mixed solution of phosphorus oxychloride and DMF. The mixture was then stirred at 90° C. for 2 h under a nitrogen atmosphere. Then the mixture was cooled to room temperature and added to 200 mL ice-water mixture. NaOH was slowly added to the reaction flask with stirring during which time a homogeneous solution was obtained followed by the precipitation of the product. The solids were collected by filtration and washed thoroughly with water and dried to give a pale-yellow solid powder in a crude yield 39%.

2 mmol of the intermediate A 1-hydroxyethyl-4-methylquinoline quaternary ammonium salt and the intermediate synthesized previously were added, then the mixture was heated to 180° C. for 30 min under a nitrogen atmosphere and then allowed to cool. The mixture was purified by silica flash column chromatography using DCM/methanol(100:8) as an eluting solvent, and the red fraction was collected to obtain the title compound in a yield of 35%.

Product analysis: $^1$H NMR (400 MHz, DMSO) δ 8.48 (d, J=8.5, 1H), 8.31 (d, J=7.1, 1H), 8.15 (m,=2H), 7.94 (d, J=7.7, 1H), 7.88 (d, J=12.0, 2H), 7.78-7.66 (m, 1H), 7.59 (s, 1H), 7.50 (t, J=7.9, 1H), 7.13 (d, J=13.4, 1H), 6.48 (d, J=12.4, 1H), 5.12 (t, J=5.1, 1H), 4.65 (t, J=4.8, 2H), 3.82 (d, J=4.7, 2H), 3.73 (s, 3H).

EXAMPLE 5

Synthesis of Compound E

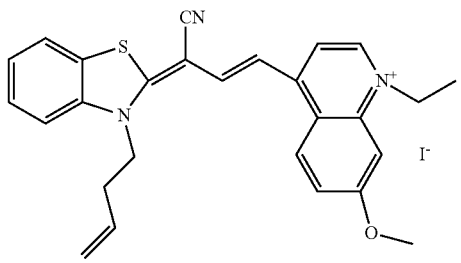

10 mmol of 1-butene-2-methylsulphenyl benzothiazole quaternary ammonium salt (1-butene-2-methylsulphenyl benzothiazole quaternary ammonium salt was synthesized with 2-methylsulphenyl benzothiazole and 4-bromo-1-butene by general synthesis method of quaternary ammonium salt similar to that described in example 1) and 10 mmol cyanoacetate were added into a round-bottom flask containing 30 mL piperidine, then the mixture was stirred to dissolve, 14 mmol triethylamine was added dropwise to the reaction solution. After overnight stirring of the resulting material, the mixture was slowly added to 300 mL water with stirring and a homogeneous solution was obtained followed by the precipitation of the product. The precipitate is filtered and the filter cake is washed with water and dried to give a khaki solid powder in a crude yield of 73%.

A 6 mmol amount of phosphorus oxychloride was added dropwise to 10 mL dimethylformamide (DMF) in an ice bath. A solution of 5 mmol of khaki intermediate synthesized previously in 10 mL DMF was added dropwise to the mixed solution of phosphorus oxychloride and DMF. The mixture was then stirred at 90° C. for 2 h under a nitrogen atmosphere. Then the mixture was cooled to room temperature and added to 200 mL ice-water mixture. NaOH was slowly added to the reaction flask with stirring during which time a homogeneous solution was obtained followed by the precipitation of the product. The solids were collected by filtration and washed thoroughly with water and dried to give a pale-yellow solid powder in a crude yield 43%.

2 mmol of 1-ethyl-4-methyl-7-methoxyquinoline quaternary ammonium salt (1-ethyl-4-methyl-7-methoxyquinoline quaternary ammonium salt was synthesized with 4-methyl-7-methoxyquinoline and ethyl iodide by general synthesis method of quaternary ammonium salt similar to that described in example 1) and the intermediate synthesized above were added, then the mixture was heated to 180° C. for 30 min under a nitrogen atmosphere and then allowed to cool. The mixture was purified by silica flash column chromatography using DCM/methanol(100:8) as an eluting solvent, and the red fraction was collected to obtain the title compound in a yield of 37%.

Product analysis: [1] NMR (400 MHz, CDCl$_3$) δ 8.98 (s, 1H), 7.86 (s, 1H), 7.70-7.35 (m, 4H), 6.91 (s, 1H), 6.85 (s, 1H), 6.68 (d, J=6.0 Hz, 2H), 5.80 (s, 1H), 5.02 (d, J=10.2 Hz, 2H), 4.80 (s, 2H), 3.89 (s, 3H), 3.62 (s, 1H), 3.53 (s, 1H), 2.30 (s, 2H), 1.61 (s, 3H).

EXAMPLE 6

Comparisons of the Photofading of Compounds C, D, E and Reference Compound M1

$5 \times 10^{-6}$ M solutions of compounds C, D, E and reference compound M1 in Tris-HCl (10 mM, pH=7.4, same below) buffer were be sealed into the cuvettes respectively. To absorb short wavelength light (<400 nm), a trap of glass containing 50 g/L NaNO$_2$ was set up between the cells and the lamp. In the other hand, NaNO$_2$ solution can be used as a cold trap to keep the sample at room temperature. After the absorption of samples were monitored, solutions of the samples were irradiated with a 500 W iodine-tungsten lamp. The distance between the cells and the lamp was 20 cm. The irreversible bleaching of the dyes at the absorption peak was monitored as a function of time at 1 hour intervals. The equipment used is a UV-Vis spectrophotometer Lambda 8453. As shown in FIG. 1, compounds C, D, and E remain 90% in optical density, while reference compound M1 remains substantially 0 after 6 h of radiation.

The result shows that asymmetric cyanines by adding a CN group to the trimethine chain C, D, and E possess much better photostability than reference compound M1.

EXAMPLE 7

Determinations of the Absorption and Fluorescence Emission Spectra of Compounds C, D, and E in the Absence and Presence of DNA Respectively in Buffer Solution 2 μM solutions of compounds C, D, and E in Tris-HCl (10 mM, pH=7.4, same below) buffer were be added into the cuvettes and determined its absorption respectively. The exited wavelength of the fluorescence spectra was 550 nm for all compounds. A saturated amount of CT DNA was added into the above solution, then the solution was determined its absorption respectively. The exited wavelength of the fluorescence spectra was 550 nm for all compounds. The equipments used are a UV-Vis spectrophotometer (Hp8453) and a spectrofluorophotometer (PTI-700).

Figure 2:
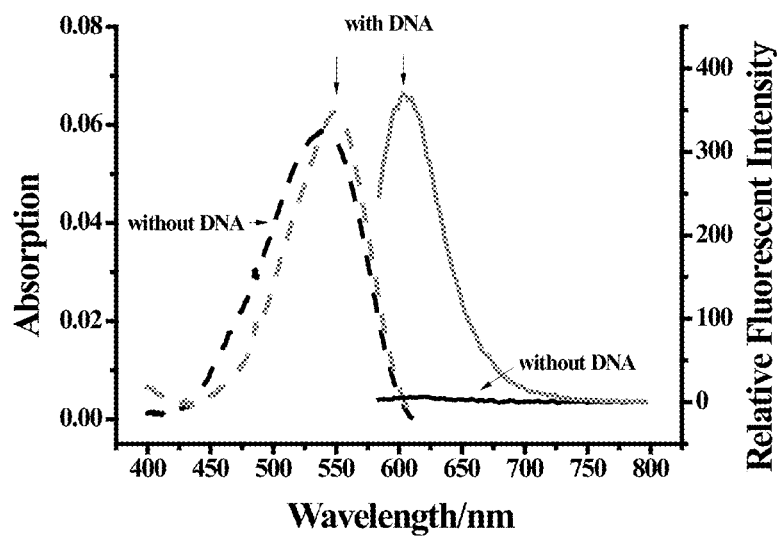
FIG. 2 is the absorbance and emission spectra of compound C in example 7 in the absence and presence of DNA in Tris-HCl buffer.
Figure 3:
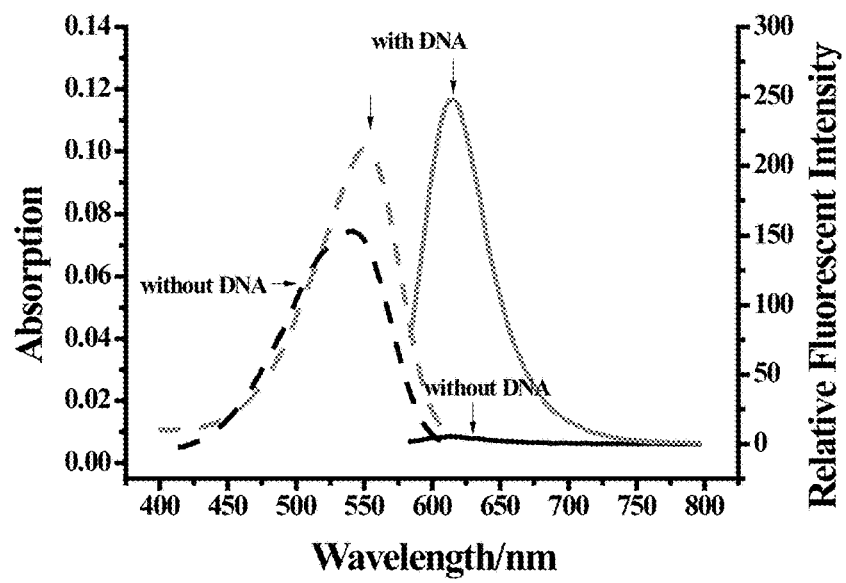
FIG. 3 is the absorbance and emission spectra of compound D in example 7 in the absence and presence of DNA in Tris-HCl buffer.
Figure 4:
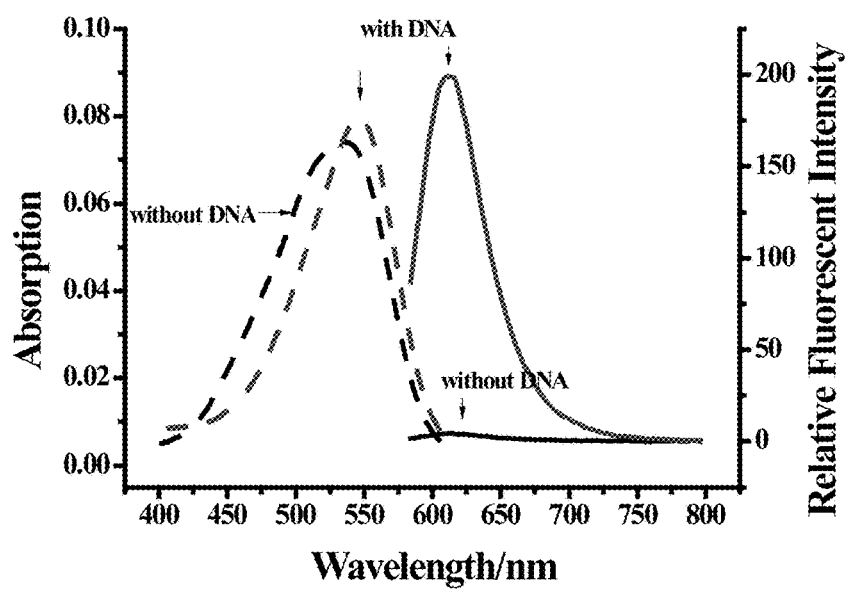
FIG. 4 is the absorbance and emission spectra of compound E in example 7 in the absence and presence of DNA in Tris-HCl buffer.

FIGS. 2, 3, and 4 are the absorption and fluorescence emission spectra of compounds C, D, and E in the absence and presence of DNA respectively in buffer solution respectively. As shown in FIGS. 2, 3, and 4, the maximum absorption wavelength of compounds C, D, and E is about 545 nm and the maximum emission wavelength is about 610 nm. Therefore, in confocal fluorescence image tests of compounds, the exited wavelength is selected 559 nm and the collected emission wavelength was 575-625 nm.

EXAMPLE 8

Determinations of the Fluorescence Quantum Yield of Compound C in the Presence of DNA A saturated amount of CT DNA was added into the 1 μM compound C solution in Tris-HCl buffer to keep a maximum absorbance less than 0.1 as determined by a UV-Vis Spectrophotometer. Fluorescence intensities are measured at selected excitation wavelengths of 545 nm, 550 nm and 555 nm, respectively. For each compound, the determination is made in triplicate, the fluorescence quantum yield of each determination is calculated, and the mean value is taken. Using Rhodamine B as the standard ($\Phi_F$=0.97, methanol, 15° C.), the calculated fluorescence quantum yields in buffer solution of compound C in the presence of DNA is 0.73. The equipments used are a UV-Vis spectrophotometer (Hp8453) and a spectrofluorophotometer (PTI-700).

EXAMPLE 9

Determinations of the Fluorescence Quantum Yield of Reference Compound M1 in the Presence of DNA A saturated amount of DNA was added into the 1 μM reference compound M1 solution in Tris-HCl buffer to keep a maximum absorbance less than 0.1 as determined by a UV-Vis Spectrophotometer. Fluorescence intensities are measured at selected excitation wavelengths of 585 nm, 590 nm and 595 nm, respectively. For each compound, the determination is made in triplicate, the fluorescence quantum yield of each determination is calculated, and the mean value is taken. Using Rhodamine B as the standard ($\Phi_F$=0.97, methanol, 15° C.), the calculated fluorescence quantum yields in buffer solution of reference compound M1 in the presence of DNA is 0.16. The equipments used are a UV-Vis spectrophotometer (Hp8453) and a spectrofluorophotometer (PTI-700).

As shown by comparing the results of examples 8 and 9, asymmetric cyanines C by adding a CN group to the trimethine chain possesses much higher fluorescence quantum yields than reference compound M1 that without the CN group.

EXAMPLE 10

Fluorescence Imaging of Live Cells Stained with Compound D or Reference Compound M1

Figure 5:
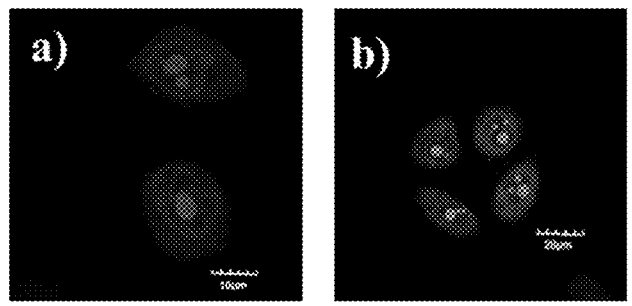
FIG. 5 is the fluorescence image of live cells stained with compound D and reference compound M1 in example 10. 5a is the fluorescence image of cells incubated with reference compound M1 at the final concentration of 3 μM for 45 min at 37° C.; 5b is the fluorescence image of cells incubated with compound D the final concentration of 2 μM for 45 min at 37° C.

MCF7 cells (human breast adenocarcinoma cell line) were cultured in DEME medium supplemented with 10% fetal bovine serum at 37° C. in an atmosphere containing 5% $CO_2$ for 24 h. For live cell imaging, compound D (2 μM) or reference compound M1 (3 μM) was added to cells for 45 min and washed with PBS (phosphate-buffered saline) three times. After replacement of the medium, cells were imaged using a confocal fluorescence microscope. As shown in FIG. 5, compound D and reference compound M1 have a good live cell membrane permeability and show clear nucleolar staining as well as faint nucleus staining. The confocal laser scanning microscope is Olympus FV1000.

EXAMPLE 11

Colocalization Fluorescence Imaging of Cells Stained with Compound E and Available Commercial Nucleic Acid Stain The cells were cultured as shown example 10, were first cultured with 3.0 μM of available commercial nucleic acid stain SYTO9 for 45 min, and then washed with PBS three times. Cells were then incubated with compound E (2.0 μM) for 45 min, and then washed with PBS three times. After replacement of DEME medium, cells were imaged using confocal fluorescence microscope.

Figure 6:
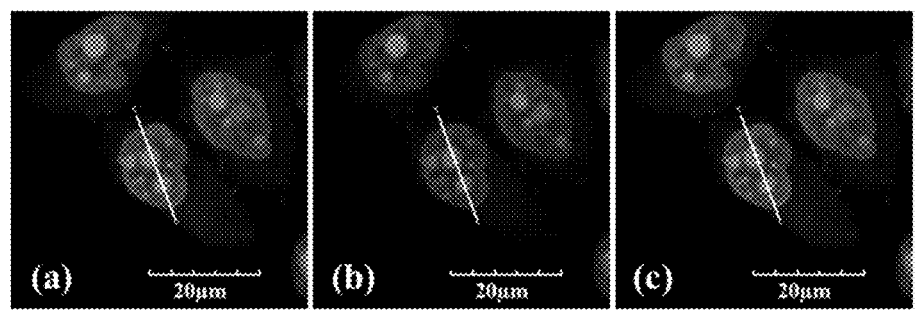
FIG. 6 is the colocalization fluorescence imaging of cells stained with compound E and available commercial nucleic acid stain SYTO9 in example 11. 6a is the fluorescence image of cells stained with SYTO 9. 6b is the fluorescence image of cells stained with compound E. 6c is the merged image of FIGS. 6a and 6b.

FIG. 6a is the fluorescence image of SYTO 9 ($\lambda_{ex}$=488 nm, $\lambda_{em}$=500 nm to 550 nm) and FIG. 6b is the fluorescence image of compound E ($\lambda_{ex}$=559 nm, $\lambda_{em}$=575 nm to 625 nm). As shown in FIG. 6c the merged image of FIGS. 6a and 6b, the same nuclear regions are labeled by compound E and available commercial nucleic acid stain SYTO9 to prove that the subcellular in cell stained with compound E are nucleus and nucleolus. The equipment used is an Olympus FV1000 confocal laser scanning microscope.

EXAMPLE 12

Figure 7:
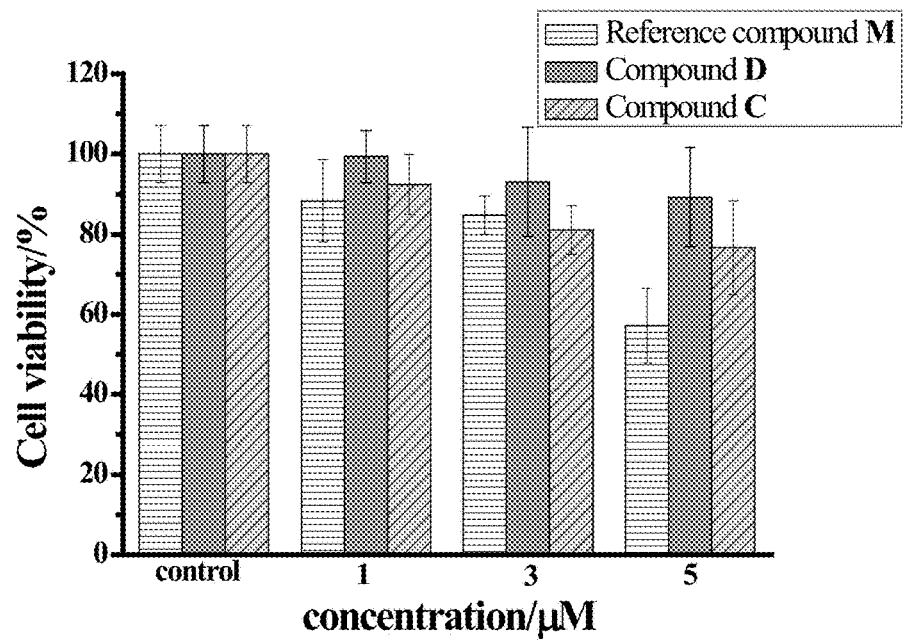
FIG. 7 is the comparisons of the cytotoxicity of compounds C, D and reference compound M1 in living cells by the MTT cytotoxicity assay.

Comparisons of the Cytotoxicity of Compounds C, D and Reference Compound M1 in Living Cells The Compounds C, D, E and reference compound M1 at serial concentrations (0, 1, 3, and 5 μM) were added to cells counted in a confocal microscope dish for 6 h. Then MTT tetrazolium solution (100 μL of 0.5 mg/ml in PBS) was added to each well, and the cells further incubated for 2 h. Excess MTT tetrazolium solution was then carefully removed and the colored formazan was dissolved in dimethyl sulfoxide (DMSO). The absorbance was measured at 490 nm using a microplate reader to measure the toxicity of compound. As shown in FIG. 7, compounds C, D and reference compound M1 have low cytotoxicity in low concentrations, but compounds C and D were less cytotoxic than reference compound M1 in high concentration. The result shows that compound by adding CN group to the trimethine chain possesses lower cytotoxicity.

The invention claimed is:

1. A dye of Formula I:

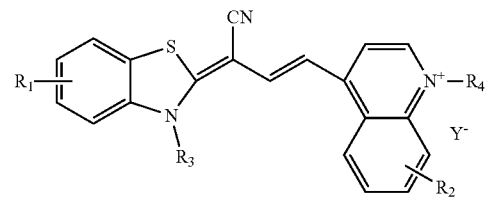

wherein $R_1$ and $R_2$ are each independently selected from the group consisting of H, $C_{1-18}$ saturated/unsaturated alkyl, $OR_5$, and halogen;

$R_3$ and $R_4$ are each independently selected from the group consisting of $C_{1-6}$ saturated/unsaturated alkyl and —$CH_2CH_2OR_5$;

$R_5$ is selected from the group consisting of H and $C_{1-6}$ alkyl; and $Y^-$ is a halogen ion.

2. The dye of claim 1, wherein $R_1$ and $R_2$ are each independently selected from the group consisting of H, $OR_5$, and halogen; $R_3$ and $R_4$ are each independently selected from the group consisting of $C_{1-4}$ saturated/unsaturated alkyl and —$CH_2CH_2OR_5$; and $R_5$ is selected from the group consisting of H and $C_{1-2}$ alkyl.

3. The dye of claim 2, wherein $R_3$ is selected from the group consisting of $C_{1-4}$ saturated alkyl and —$CH_2CH_2CH=CH_2$.

4. The dye of claim 2, wherein $R_4$ is selected from the group consisting of $C_{1-2}$ alkyl and —$CH_2CH_2OH$.

5. The dye of claim 1, selected from the group consisting of C, D and E:

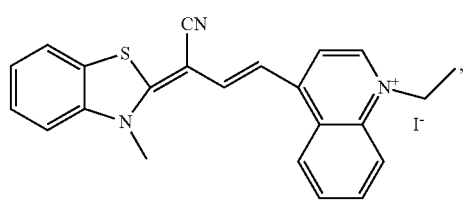

-continued
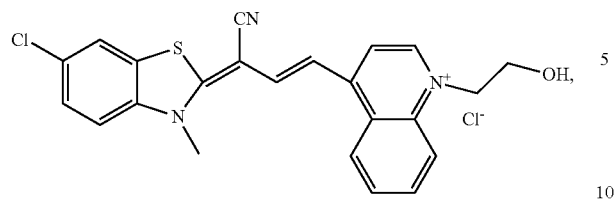
D
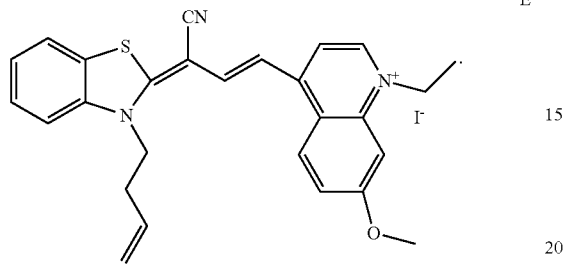
E
* * * * *